United States Patent [19]
Riley et al.

[11] Patent Number: 5,925,348
[45] Date of Patent: Jul. 20, 1999

[54] METHODS UTILIZING COMPOSITIONS CONTAINING SACRED LOTUS (METHYLTRANSFERASE) TO TREAT AGING SKIN

[75] Inventors: Patricia A. Riley; Thomas Babcock, both of Sunrise, Fla.

[73] Assignee: Medical Doctor's Research Institute, Inc., Sunrise, Fla.

[21] Appl. No.: 08/804,230

[22] Filed: Feb. 21, 1997

Related U.S. Application Data

[60] Provisional application No. 60/012,158, Feb. 23, 1996.
[51] Int. Cl.$^6$ .............................. A61K 38/45; A61K 7/48
[52] U.S. Cl. ..................... 424/94.5; 424/195.1; 424/401; 514/844; 514/859
[58] Field of Search ..................................... 424/401, 450, 424/464, 489, 69, 451, 94.5, 195.1; 514/844, 847, 859, 937, 938, 944; 435/193; 549/315; 530/332

[56] References Cited

U.S. PATENT DOCUMENTS

| Re. 33,993 | 7/1992 | Grollier et al. |  |
|---|---|---|---|
| 367,337 | 7/1887 | Carson et al. |  |
| 5,190,762 | 3/1993 | Yarosh | 424/450 |
| 5,272,079 | 12/1993 | Yarosh | 435/193 |
| 5,296,231 | 3/1994 | Yarosh | 424/450 |

FOREIGN PATENT DOCUMENTS

| 1090129 | 4/1986 | Japan. |
| 3-190809 | 8/1991 | Japan. |
| 0424012 | 9/1992 | Japan. |

OTHER PUBLICATIONS

McFadden et al. Methylation at D–Aspartyl Residues in Erythrocytes: Possible Step in the Repair of Aged Membrane Proteins. Proc. Natl. Acad. Sci. USA 79(Apr. 1992) pp. 2460–2464.

McFadden et al. Protein Carboxyl Methyltransferase and Methyl Acceptor Proteins in Aging and Cataractous Tissue of the Human Eye Lens. Mechanisms of Ageing & Development, 34(1986) 91–105.

Mukherjee et al., Indian Journal of Pharmacology, (27) 262–264, 1995.

MacLaren et al., Protein Expression and Purification, (6) 99–108, 1995.

Danhof, Phytotherapy Research, vol. 7, S53–S56, 1993.

Fox, Cosmetics and Toiletries, V. 109, n9, p. 83(22), 1994.

Rieger, Cosmetics and Toiletries, V. 107, n11, p. 85(9), 1992.

Clarke, Journal of Cellular Biochemistry, Suppl. 17D, 145, 1993.

Mudgett et al., Biochemistry, vol. 32, 11100–11111, 1993.

Mizobuchi et al., Journal of Neurochemisry, vol. 62 (1), 322–328, 1994.

Shen–Miller et al., American Journal of Botany, 82 (11) 1367–1380, 1995.

*Primary Examiner*—Robert H. Harrison
*Attorney, Agent, or Firm*—Holland & Knight LLP

[57] ABSTRACT

Cosmetic, dermatological and dietary compositions for treatment of aging of the skin are provided that contain an extract of the Sacred Lotus (Nelumbo Nucifera) seed as an active anti-aging agent in a suitable carrier or vehicle along with methods of treatment to reduce signs of aging such loss of elasticity, age spots, acne, blemishes, enlarged pores, fine lines, wrinkles and to promote overall younger looking skin by using said compositions.

14 Claims, 6 Drawing Sheets

Fig. 1

NECK/BEFORE

NECK/AFTER

LEFT HAND/BEFORE
RIGHT HAND/AFTER

LEFT HAND/BEFORE
RIGHT HAND/AFTER

Fig. 2

BEFORE

AFTER

BEFORE

AFTER

BEFORE

AFTER

BEFORE

AFTER

Fig. 3

BEFORE   AFTER

BEFORE   AFTER

Fig. 4

BEFORE    AFTER

BEFORE    AFTER

Fig. 5

BEFORE    AFTER

IMPROVEMENT IN ELASTICITY

FIG. 6

METHODS UTILIZING COMPOSITIONS CONTAINING SACRED LOTUS (METHYLTRANSFERASE) TO TREAT AGING SKIN

CROSS REFERENCE TO A RELATED APPLICATION

This application for U.S. patent is a U.S.C., Title 35, §111(a) application which is based on a co-pending U.S.C., Title 35, §111(b) U.S. provisional application, Serial No. 60/012,158. Therefore, pursuant to 37 CFR §1.78(c), reference is made to and priority is claimed from U.S. provisional application, Serial No. 60/012,158, which was filed on Feb. 23, 1996, which is pending and which is entitled "Methods & Micronutrient Compositions for use as Nutritional Supplements."

FIELD OF THE INVENTION

The present invention relates to the use of Sacred Lotus seed extract in a cosmetic, dermatological and/or dietary compositions for combating aging and methods for treatment and prevention of aging using such compositions. The present invention also concerns the use of components of the Sacred Lotus plant, such as methyltransferase and especially L-isoaspartyl methyltransferase, ascorbic acid, glutathione, etc.

BACKGROUND

Within the dermis are highly stable fibers of collagen and elastin. Collagen, the most abundant protein in the body, has a high tensile strength thus preventing skin from being torn by over stretching. Elastin, also a protein, allows movement. As skin ages elastic tissue increases but it loses the ability to stretch and recover. This loss of resiliency and elasticity is accompanied by increased stiffness, sagging and wrinkling. Changes in collagen solubility and cross-linking contribute to loss of elasticity.

On the cellular level, aspartyl and asparaginyl residues are prominent sites of age related damage in proteins. These damaged sites have been characterized in a variety of proteins, but are particularly common in the long-lived proteins. Enzymatic mechanisms for reversing damage to DNA are well established and have been shown to be essential for extended lifespan.

Experiments performed in vitro with recombinant and chemically modified polypeptides have shown that the presence of an L-isoaspartyl residue may alter both enzymatic activity and the binding of other molecules.

Limiting the accumulation of these residues within cells is currently believed to be important; all human cells examined thus far contain an L-isoaspartyl/D-aspartyl protein methyltransferase that has been proposed to serve this function. It is also believed that this methyltransferase can recognize both D-aspartyl and L-isoaspartyl residues. In addition, it is thought that this enzyme may have the ability to reverse at least part of the damage to protein molecules.

Although the human isoaspartyl protein repair methyltransferase has been purified from red blood cells and had its protein sequence determined, in addition to harvesting a variant in a bacterial system, the availability and use of methyltransferases has been limited.

On or around Nov. 14, 1995, however, it was reported that scientists germinated a 1,288 year old Sacred Lotus seed. The research reported in the November issue of the American Journal of Botany, began in 1982, when Jane Shen-Miller, a plant physiologist at the University of California at Los Angeles (UCLA), obtained seven brown, oval-shaped Sacred Lotus seeds from the Beijing Institute of Botany.

In 1983, Jane Shen-Miller filed through the hard shells of four of the ancient Sacred Lotus seeds and watched three of them sprout. She then dried and burned the seedlings so she could use radiocarbon dating to establish the ages, the oldest of which was 1,288 years old.

According to the November, 1995 report, one of those ancient Sacred Lotus seeds had been in the ground for over 1,200 years; it therefore has been postulated that the Sacred Lotus seeds act as embryos that must be kept going until such seeds are germinated. Up until this point, geneticists knew only about proteins that repaired damaged DNA. But findings have suggested that the L-isoaspartyl methyltransferase (MT) enzyme, found in the Sacred Lotus seeds and nearly all other organisms, may have the ability to repair other proteins—those that make up cells and tissues, thus slowing tissue decay.

In these ancient Sacred Lotus seeds, the MT enzyme was present at levels comparable to modern day Sacred Lotus seeds. Damaged proteins did not accumulate within the ancient Sacred Lotus seeds, suggesting that the MT enzyme, possibly along with other constituents, kept the ancient Sacred Lotus seeds alive for so many years.

Notwithstanding the above, it is unknown as to whether use of methyltransferase or extracts or components of the Sacred Lotus plant in topical or oral compositions would be effective in combatting aging, repairing damaged skin and/or restoring skin to a more youthful appearance. Moreover, there are no known acceptable products available which incorporate methyltransferase or extracts or components of the Sacred Lotus for combatting dermatological aging, repairing damaged skin and/or restoring skin to a more youthful appearance.

Consequently, there exists a need for acceptable delivery systems which incorporate methyltransferase or extracts or components of the Sacred Lotus plant for effectively treating and preventing aging, repairing damaged skin and restoring skin to a more youthful appearance.

SUMMARY OF THE INVENTION

In brief, the present invention alleviates and overcomes certain of the above-mentioned problems and shortcomings of the present state of the art through the discovery of novel acceptable delivery systems which embody methyltransferase or extracts or components of the Sacred Lotus plant for effectively treating and preventing aging, repairing damaged skin and restoring skin to a more youthful appearance and methods of using same.

Accordingly it is the object of the invention to provide a general method for prevention or alleviation of damage to the skin associated with aging through the topical and/or internal use of methyltransferase in combination with a suitable carrier or vehicle.

Another object is to restore the skin to a more youthful appearance.

Another object is to use the extract of the Sacred Lotus (Nelumbo nucifera) seed as a natural source of methyltransferase. It has now been observed, surprisingly and unexpectedly, that by using an extract of the Sacred Lotus seed by topical application as an active agent, signs of aging can be reduced, eliminated or even reversed.

Also until the present invention there were no acceptable vehicles utilizing methyltransferase from a natural source such as lotus seed and its other natural components in an elegant cosmetic and/or basic pharmaceutical composition and/or dietary formulation. Thus, another object of the present invention are formulations of Sacred Lotus seed in dermatologicals, such as lotions, creams, sunscreens, cleansers, and various skin care formulas to improve the youthful appearance of the skin, repair visible damage, and reduce the signs of aging including loss of elasticity, fine lines, wrinkles, blemishes, spots and discolorations.

Another object is the formulation of dietary supplements providing the anti-aging benefits of methyltransferase and antioxidants found in the Sacred Lotus seeds.

A suitable carrier or vehicle will include the formulation of creams, gels, lotions, powders, tablets, capsules, and liquid preparations for the skin to repair the damage from aging, reduce further damage and restore skin to a more youthful appearance.

These and other objects are achieved by the present invention which is directed to a topical or oral formulation for the protection of the skin against damage caused by aging and a method for preventing or alleviating such damage and restoring it to a more youthful appearance by employing such in a topical or oral formulation.

The formulation is a suitable cosmetic or dermatologically or orally acceptable non-toxic, non-allergenic carrier containing methyltransferase and other components of the seed or of the sacred lotus plant.

The above features and advantages of the present invention will be better understood with reference to the accompanying FIGS., detailed description and examples. It should also be understood that the particular methods and formulations illustrating the present invention are exemplary only and not to be regarded as limitations of the present invention.

BRIEF DESCRIPTION OF THE DRAWINGS

Reference is now made to the accompanying FIGS. in which is shown illustrative results of exemplary embodiments of the present invention from which its novel and unique features and advantages will be apparent.

FIG. 6 depicts before and after results on facial skin around the mouth following administration of one of the topical compositions set forth in Examples 2–6.

DETAILED DESCRIPTION

By way of illustrating and providing a more complete appreciation of the present invention and many of the attendant advantages thereof, the following detailed description and examples are given concerning the novel delivery systems which embody methyltransferase or extracts or components of the Sacred Lotus plant for effectively treating and preventing aging, repairing damaged skin and restoring skin to a more youthful appearance and methods of using same.

The present invention uses Sacred Lotus Seed extract in skin and dietary formulas to combat aging. It is believed that the use of Sacred Lotus seeds in cosmetics and dietary supplements accomplish anti-aging effects based on anti-aging factors (enzymes such as methyltransferase) which are present in the seeds.

Moreover, Sacred Lotus seeds contain certain antioxidants such as vitamin C and glutathione which may contribute to anti-aging effects on skin along with methyltransferase and may even contain other beneficial factors.

In accordance with the present invention, methyltransferase and/or the natural compounds found in an extract of Sacred Lotus seeds may be used in an effort to repair age related signs of the skin such as lines, spots, wrinkles, and/or loss of elasticity. Other sources of methyltransferase that may be used in the invention are components of Sacred Lotus plants, extracts of Yellow Lotus seeds or components of Yellow Lotus plants, wheat germ oil, liver, brain, testes and bio-fermentation or chemical synthesis for example.

An extract is prepared, for example, as follows. Maceration is the preferred process since no heat is used which may destroy or alter temperature sensitive components; however percolation, digestion, infusion and decoction are within the scope of the invention as more scientific information becomes available.

A twenty percent extract of NELUMBO NUCIFERA is generally used and prepared by placing 200 grams of finely milled untreated whole seeds, including husks and pithes, in a stoppered container with about 750 ml of a 50/50 wt/wt mixture of purified water and propylene glycol U.S.P. and allowed to stand for a period of at least 3 days in a warm place with frequent agitation, until soluble matter is dissolved. The mixture is filtered and, after most of the liquid has drained, the residue on the filter is washed with sufficient quantity of the solvent mixture; the filtrates are combined to produce 1000 ml.

It is also within the scope of the present invention to use different amounts of the seed, other parts of the plant as well as other species solvents and mixtures.

While it is believed that Sacred Lotus "Nelumbo nucifera" is a preferred species and the seed is a preferred part, other parts of the plant or other species, such as the Yellow Lotus "Nelumbo lutea," containing these "anti-aging" enzymes or constituents are believed to be suitable alternatives for accomplishing the objectives of the present invention.

A composition according to the present invention for topical application contains an effective amount of the anti-aging agent Sacred Lotus seed extract from 0.05% to 100% by weight of the extract relative to the total weight of the composition, and preferably from 0.10% to 10% concentration by weight. It should be understood that the topical compositions may be used at any appropriate daily intervals, depending of course upon the particular type of composition formulated. For instance, the night serum, as set forth in Example 3 hereinafter, is to be administered once-a-day at night after proper cleansing, whereas the wrinkle serum of Example 2 may be administered twice-a-day in the morning and evening. The spot-lightening formulation of Example 4, on the other hand, may be applied, after cleansing, initially on a daily basis for about 6 to 8 weeks, at which time fading will gradually occur. Administration then may be reduced to only 1 to 2 times per week, after cleansing, to prevent reappearance of spots. The wrinkle alpha hydroxy formulation set forth in Example 6 may be applied once or twice daily following cleansing; however, if dryness occurs, use of this product may be reduced to 1 to 3 times per week.

A composition according to the present invention for oral administration contains an effective amount of the anti-aging agent Sacred Lotus seed (with husk, shell and plumele) from 0.01% to 100% by weight of the ground seed or 0.05% to 100% by weight of the extract relative to the total weight of the composition, and preferably 0.03% to 0.05% of the Sacred Lotus seed concentration by weight (300 mcg to 500 mcg per 840 mg tablet or capsule). More particularly, and by way of example, an oral composition containing ground Sacred Lotus seed can be prepared as follows. The whole Sacred Lotus seed with husk, shell and plumele (pith or embryo), supplied by W.T.H., 130 Wing Lok St., 8/F, Hong Kong, is first ground through a coffee mill having a fine screen (#24 Mesh or 700 microns particle size). The ground seeds are than treated with ionizing radiation with an absorbed dose from about 7.19 kGy minimum to 7.69 kGy maximum for sterilization purposes. The irradiated ground seeds may then be powder blended with other selected components to formulate oral delivery systems in accordance with the present invention, as discussed in greater detail hereinafter.

A composition according to the present invention may be in any of the cosmetic or pharmaceutical forms which are generally used for topical application such as liquids (both aqueous and non-aqueous solutions), creams (both oil-in-water and water-in-oil, O/W & W/O emulsions), gels (both aqueous and non-aqueous), lotions, serums, ointments, paste, powders, liposomes, laminates, microspheres, tablets and powders.

An oral composition according to the present invention may be in any of the dosage forms which are generally used for dietary supplements such as liquids, gels, powders, tablets, caplets, capsules and soft gels. While it is generally preferable to formulate the oral dosages to each contain, for example, about 350 mcg of Sacred Lotus seed for administration twice daily, it should be understood that any effective dosage strength may be formulated for administration at any effective daily interval, so long as the objectives of the instant invention are not defeated.

Compositions of the present invention may also contain additives, such as water, alcohols, oils (mineral, vegetable, animal and synthetics), glycols, colorants, preservatives, emulsifiers, gelling agents, gums, esters, hormones, antioxidants, silicones, polymers, fragrances, flavors, sunscreens, other active ingredients, antioxidants, acids, bases, buffers, vitamins, minerals, salts, polyols, proteins and their derivatives, essential oils, other enzymes, co-enzymes and extracts, surfactants, detergents, soaps, anionics, non-ionics, ionics, waxes, lipids, UV filters, stabilizers, fillers, celluloses, glycans, amines, solubilizers, thickeners, sugars and sugar derivatives, ceramides, sweeteners and the like, so long as such additives do not defeat the objectives of the present invention.

A composition according to the present invention as an effective anti-aging agent may be employed alone, that is without the use of additional actives, or the Sacred Lotus seed may be used to enhance other ingredients. Moreover, it should be understood by those versed in this art that the present invention contemplates treating the skin with either the topical compositions or the oral compositions of the instant invention or concommitantly with both types of compositions. It is believed that when both the oral and topical compostions of the present invention are administered, such combination therapy will promote both good health and radiant skin, especially when the oral compostions include micronutrients, such as in the oral composition set forth in Example 7 hereinafter.

One preferred composition combines the Sacred Lotus seed with glycocyamine, hyaluronic acid, and alpha hydroxy acids for their role in glycosaminoglycan (a protein sugar complex essential for normal hydration in the skin) synthesis plus antioxidants, such as vitamins A, C and E, extracts of pine bark, grape seed and green tea, catalase, superoxide dismutase and coenzyme Q-10 to protect the skin from free radicals and alleviate further cellular damage.

Other items such as lecithin, squalene, panthenol, vitamin D3, jojoba oil, olive oil, glycerin and other moisturizers also appear to benefit with the addition of Sacred Lotus seed in providing moisture into the skin enhancing its repair process, promoting elasticity and making the skin appear younger.

Hydroquinone, sulfur and salicylic acid also appear to exhibit synergism with Sacred Lotus Seed extract.

The following examples are given for illustrative purposes only to delineate some of the features of the invention and are not intended to be limiting. As to exemplary formulations set forth below, the quantities are given in percent by approximate weight (% wt) or approximate units (IU) unless otherwise noted based on the total weight of the composition. The term qs means to use a sufficient quantity by weight to bring the entire composition to 100%. Whenever possible International Nomenclature Cosmetic Ingredient (INCI) names are used.

EXAMPLE 1

| Anti-Aging Moisture Concentrate | |
|---|---|
| Part I: | |
| Water | 78.10 |
| Diazolidinyl Urea | 0.30 |
| Methylparaben | 0.20 |
| Part II: | |
| Hydroxyethylcellulose | 0.30 |
| Part III: | |
| Stearamidopropyl Dimethylamine Lactate | 1.50 |
| Glycerin | 2.00 |
| Cetyl Alcohol | 4.00 |
| Glycol Stearate | 3.50 |
| Propylparaben | 0.10 |
| Part IV: | |
| Sacred Lotus seed extract | 10.00 |

Procedure:

Part I is mixed and heated to 80 C. Part II is slowly added with mixing; then covered and continued mixing for 30 minutes. Part III is mixed and heated also to 80 C. Part III is then added to Part I with mixing. With continued mixing the heat is removed and cooling started. At 40 C Part IV is added. At 35 C mixing is stopped.

A thick luscious fat and oil free lotion was obtained to moisturize aged and dried skin.

EXAMPLE 2

Anti-Aging Wrinkle Serum

Part I:

| | |
|---|---|
| Water | 75.36 |
| Glycerin | 1.50 |
| Tetrasodium EDTA | 0.10 |
| Panthenol | 0.30 |
| Diazolidinyl Urea | 0.30 |
| Methylparaben | 0.25 |
| Sodium PCA | 0.50 |

Part II:

| | |
|---|---|
| Magnesium Aluminum Silicate | 0.90 |

Part III:

| | |
|---|---|
| Glyceryl Dilaurate | 0.50 |
| Sunflower Oil | 10.00 |
| Olive Oil | 2.50 |
| Cetyl Alcohol | 2.70 |
| Glyceryl Stearate PEG-100 | 3.00 |
| Propylparaben | 0.10 |

Part IV:

| | |
|---|---|
| Tocopheryl Acetate | 0.50 |
| Retinyl Palmitate | 0.05 |
| Coenzyme Q-10 | 0.01 |

Part V:

| | |
|---|---|
| Corn Oil, Glyceryl Oleate, Propylene Glycol, BHA, BHT, Propyl Gallate, and Citric Acid | 0.05 |
| Magnesium Ascorbyl Phosphate | 0.05 |
| Catalase | 0.25 |
| Superoxide Dismutase | 0.25 |
| Beta Carotene | 0.01 |
| Green Tea Extract | 0.10 |
| Grape Seed Extract | 0.10 |
| Pine Bark Extract | 0.10 |
| Sacred Lotus seed extract | 0.20 |
| 25% Sodium Hydroxide qs to pH 7.00 | 0.02 |
| Fragrance | 0.30 |

Procedure:

Part I is mixed and heated to 80 C. Part II is slowly added with mixing; then covered and continued mixing for 30 minutes. Part III is mixed and heated also to 80 C. Part III is then added to Part I with mixing. With continued mixing the heat is removed and cooling started. At 50 C Part IV is added. At 40 C Part V is added followed by fragrance. At 35 C mixing is stopped. Ph is measured and adjusted if necessary.

An enriched serum that readily dispenses from a pump to alleviate wrinkles.

EXAMPLE 3

Anti-Aging Night Serum For Dry Skin

Part I:

| | |
|---|---|
| Water | 51.62 |
| Glycerin | 2.00 |
| Tetrasodium EDTA | 0.05 |
| Panthenol | 1.50 |
| Diazolidinyl Urea | 0.20 |
| Methylparaben | 0.20 |

Part II:

| | |
|---|---|
| Hydroxyethylcellulose | 0.10 |

Part III:

| | |
|---|---|
| Propylene Glycol | 3.00 |
| Cetearyl Phosphate | 1.00 |
| Cetearyl Alcohol | 1.00 |
| DEA Cetyl Phosphate | 2.20 |
| Cetyl Alcohol | 2.00 |
| Glycol Stearate | 1.00 |
| Soybean Oil | 3.00 |
| Propylparaben | 0.10 |
| Squalene | 3.00 |
| Polysorbate 20 | 0.40 |
| Jojoba Oil | 2.00 |
| Cyclomethicone | 2.00 |
| Phenyl Dimethicone | 3.00 |
| Titanium Dioxide | 1.00 |

Part IV:

| | |
|---|---|
| Tocopheryl Acetate | 1.50 |
| Coenzyme Q-10 | 0.01 |
| Retinyl Palmitate | 0.20 |

Part V:

| | |
|---|---|
| Oat Beta Glucan | 1.00 |
| Magnesium Ascorbyl Phosphate | 0.30 |
| Catalase | 1.00 |
| Superoxide Dismutase | 2.00 |
| Beta Carotene | 0.05 |
| Green Tea Extract | 1.00 |
| Grape Seed Extract | 1.00 |
| Pine Bark Extract | 1.00 |
| Sacred Lotus seed extract | 4.00 |
| N-Acetyl Glycocyamine | 2.00 |
| Saccharide Isomerate | 2.00 |
| Sodium Hyaluronate | 2.00 |
| Histidine HCL | 0.50 |
| 25% Sodium Hydroxide qs to pH 7.00 | 0.02 |
| Fragrance | 0.25 |

Procedure:

Part I is mixed and heated to 80 C. Part II is slowly added with mixing; then covered and continued mixing for 30 minutes. Part III is mixed and heated also to 80 C. Part III is then added to Part I with mixing. With continued mixing the heat is removed and cooling started. At 50 C Part IV is added. At 40 C Part V is added followed by fragrance. At 35 C mixing is stopped. Ph is measured and adjusted if necessary.

A serum that is used at night to restore moisture to dry skin.

EXAMPLE 4

Anti-Aging Spot Lightener

Part I:

| | |
|---|---|
| Water | 91.79 |
| Hydroquinone | 2.00 |
| Ascorbic Acid | 1.00 |
| Sodium Metabisulfite | 0.15 |
| Diazolidinyl Urea | 0.30 |
| Methylparaben | 0.20 |
| N-Acetyl Glycocyamine | 1.00 |
| Citric Acid | 0.10 |

Part II:

| | |
|---|---|
| Polysorbate 20 | 2.00 |
| Fragrance | 0.20 |
| 25% Sodium Hydroxide | 0.26 |
| Sacred Lotus seed extract | 1.00 |

Procedure:

Part I is mixed until completely clear. Adjust pH of Part I to 5.50 +/−0.10 with 25% Sodium Hydroxide solution. Premix Part II and add slowly to Part I with constant mixing. When clear the Sacred Lotus Seed Extract is added and stirred until completely clear. A thin solution that is easily used from a roll-on applicator to target age spots, freckles, uneven skin tone and damage caused by the sun.

EXAMPLE 5

Anti-Aging Acne Blemish Treatment

Part I:

| | |
|---|---|
| SD Alcohol 40-B | 67.85 |
| Salicylic Acid | 2.00 |
| Sacred Lotus seed extract | 1.00 |
| Witch Hazel Distillate | 10.00 |
| Glycerin | 10.00 |

Part II:

| | |
|---|---|
| Retinyl Palmitate | 0.05 |
| Fragrance | 0.10 |
| Polysorbate 80 | 10.00 |

Procedure:

Mix Part I until completely clear keeping covered to avoid any alcohol loss. Mix Part II until uniform. Add Part II to Part I and mix until clear.

A simple topical that is effective especially on oily skin without excessive irritation.

EXAMPLE 6

Anti-Aging Alpha Hydroxy Acid Wrinkle Treatment

Part I:

| | |
|---|---|
| Water | 76.61 |
| N-Acetyl Glycocyamine | 1.00 |
| Aloe (10X conc.) | 0.20 |
| Magnesium Acorbyl Phosphate | 0.50 |
| Diazolidinyl Urea | 0.20 |
| Methylparaben | 0.10 |

Part II:

| | |
|---|---|
| Glycolic Acid 70% | 7.14 |
| Blackcurrent Extract, Bilberry Extract, Citric Acid, Glycolic Acid, Lactic Acid and Malic Acid | 1.00 |
| Sugar Cane Extract, Citric Acid, Glycolic Acid, Lactic Acid and Malic Acid | 1.00 |

Part III:

| | |
|---|---|
| Polysorbate 20 | 1.50 |
| Retinyl Palmitate | 0.05 |
| Fragrance | 0.20 |
| Tocopheryl Acetate | 0.50 |
| 25% Sodium Hydroxide | 8.00 |
| Sacred Lotus seed extract | 2.00 |

Procedure:

Part I is mixed until completely clear. Part II is also mixed until completely clear. Part II is added to Part I and mixed until clear. Adjust pH of Parts I & II to 5.00 with 25% Sodium Hydroxide solution. Premixed Part III is added and mixed until clear followed by Sacred Lotus Seed Extract addition.

A liquid combination of various alpha hydroxy acids with Sacred Lotus Seed Extract shown to be effective in reducing the appearance of lines and wrinkles. Also minimized pore size and improved the texture of the skin imparting a more youthful and radiant appearance.

EXAMPLE 7

Anti-Aging Dietary Supplement

| | | |
|---|---|---|
| Vitamin A Palmitate | 1750 | IU |
| Natural Beta Carotene | 750 | IU |
| Lycopene | 0.375 | mg |
| Lutein | 0.375 | mg |
| Vitamin E (d-alpha tocopheryl acetate and mixed tocopherols) | 50 | IU |
| Cholecalciferol | 200 | IU |
| Vitamin C | 150 | mg |
| Thiamine HCL | 4 | mg |
| Riboflavin | 5 | mg |
| Niacinamide | 20 | mg |
| Pyridoxine HCL | 6 | mg |
| Folic Acid | 200 | mcg |
| Vitamin B-12 | 5 | mcg |
| Pantothenic Acid | 7.5 | mg |
| Biotin | 75 | mcg |
| Calcium (Carbonate & Citrate) | 12.5 | mg |
| Magnesium Oxide | 18.75 | mg |
| Iron (Fumarate) | 7.5 | mg |
| Zinc (Sulfate & Gluconate) | 7.5 | mg |
| Manganese Gluconate | 2 | mg |
| Selenium (L-Selenomethionine & Citrate) | 35 | mcg |
| Chromium Nicotinate | 37.5 | mcg |
| Copper Gluconate | 0.5 | mg |
| Green Tea Extract | 7.5 | mg |
| Grape Seed Extract | 7.5 | mg |
| N-Acetyl Glycocyamine | 15 | mg |
| Citrus Bioflavanoids | 37.5 | mg |
| N-Acetyl Cysteine | 5 | mg |
| Sacred Lotus seed | 350 | mcg |
| Magnesium Stearate (Lubricant) | 8.4 | mg |
| Stearic Acid (Binder) | 42 | mg |
| Microcrystalline Cellulose (Tablet Aide) qs | 840 | mg |

Procedure:

All of the above was mixed in a powder blender until completely homogenous. The mixed powder was fed into a tablet press and compressed into tablets.

A unique blend of protective antioxidants and essential nutrients with the entire Sacred Lotus Seed (in food preparations the pithe (embryo) or plumule is removed due to bitter taste) used to promote good health and radiant skin. This product maybe taken, for example twice per day. i.e., take one tablet with breakfast and one tablet with lunch or dinner.

EXAMPLE 8

During the course of a Dermatologist's clinical study it was discovered that a lotion containing Sacred Lotus Seed extract alone resulted in a decrease in the appearance of aging sun-damaged skin on the hands. The lotion used in this Example 8 was the Anti-Aging Moisture Concentrate set forth in Example 1 above. In two participants, the lotus seed extract alone was used in a 10% concentration with either a placebo or active formulated lotion on the hands.

Figure 1:
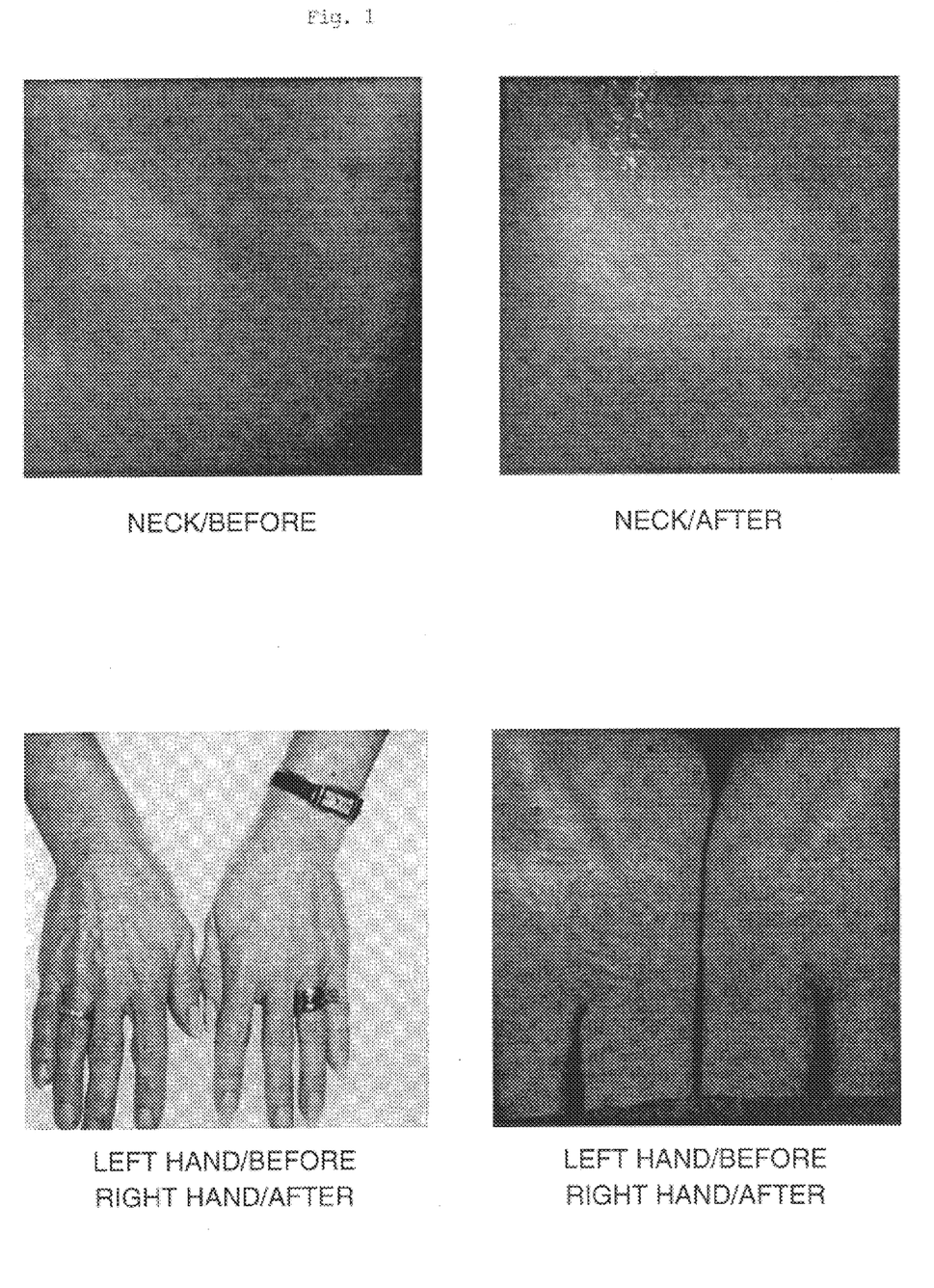
FIG. 1 depicts before and after results on a neck and hands following administration of the Anti-Aging Moisture Concentrate, as set forth in Example 1.

Side by side comparison of the treated vs. untreated hand of one participant showed obvious differences. The skin of the treated hand was more porcelain in appearance, there was reduction in fine wrinkling, dryness and the hand appeared less aged and less sun-damaged. In another participant, one hand was treated, and before and after photographs showed similar results. See FIG. 1.

EXAMPLE 9

Figure 2:
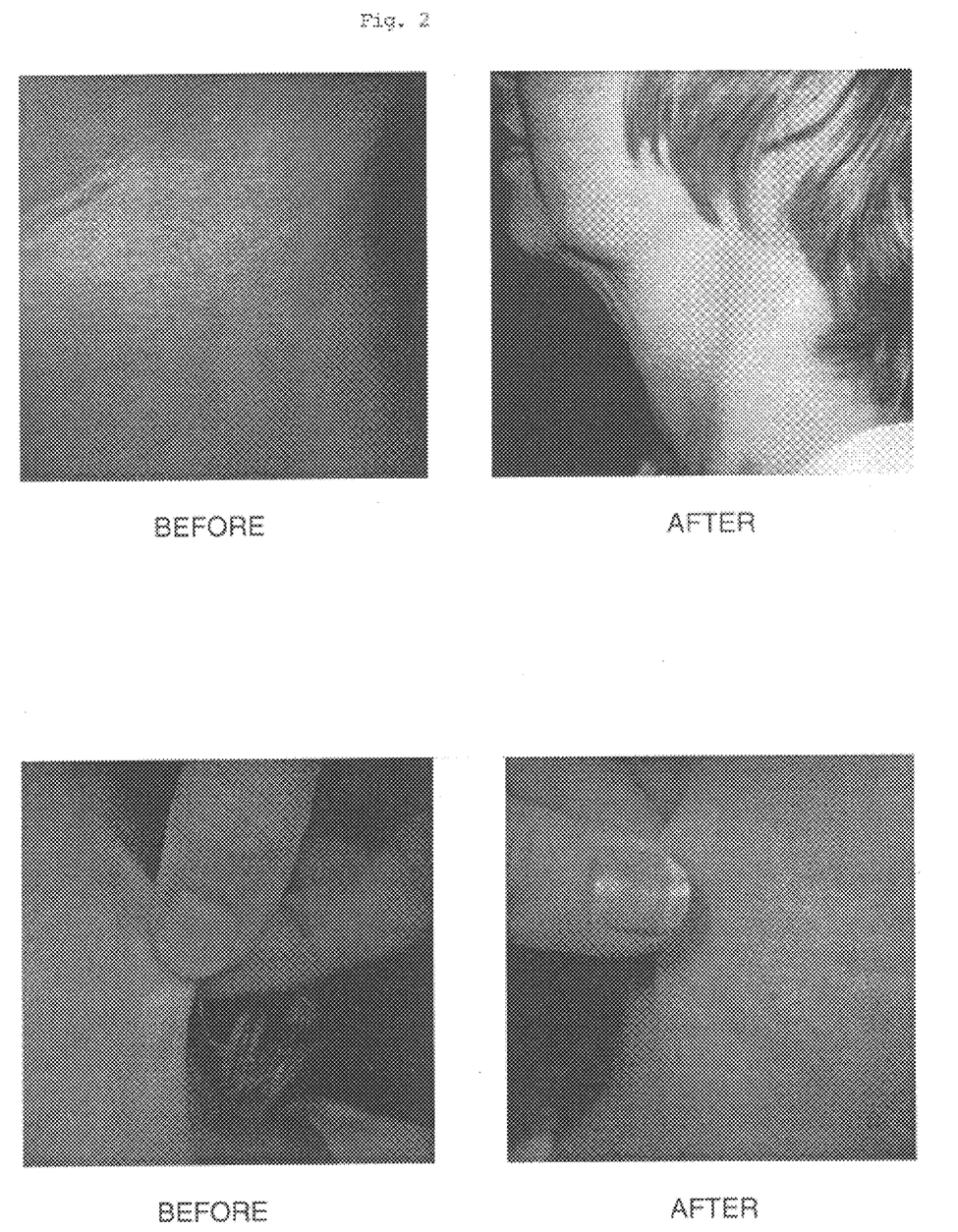
FIG. 2 likewise depicts before and after results on a neck following administration of the Anti-Aging Moisture Concentrate, as set forth in Example 1.
Figure 3:
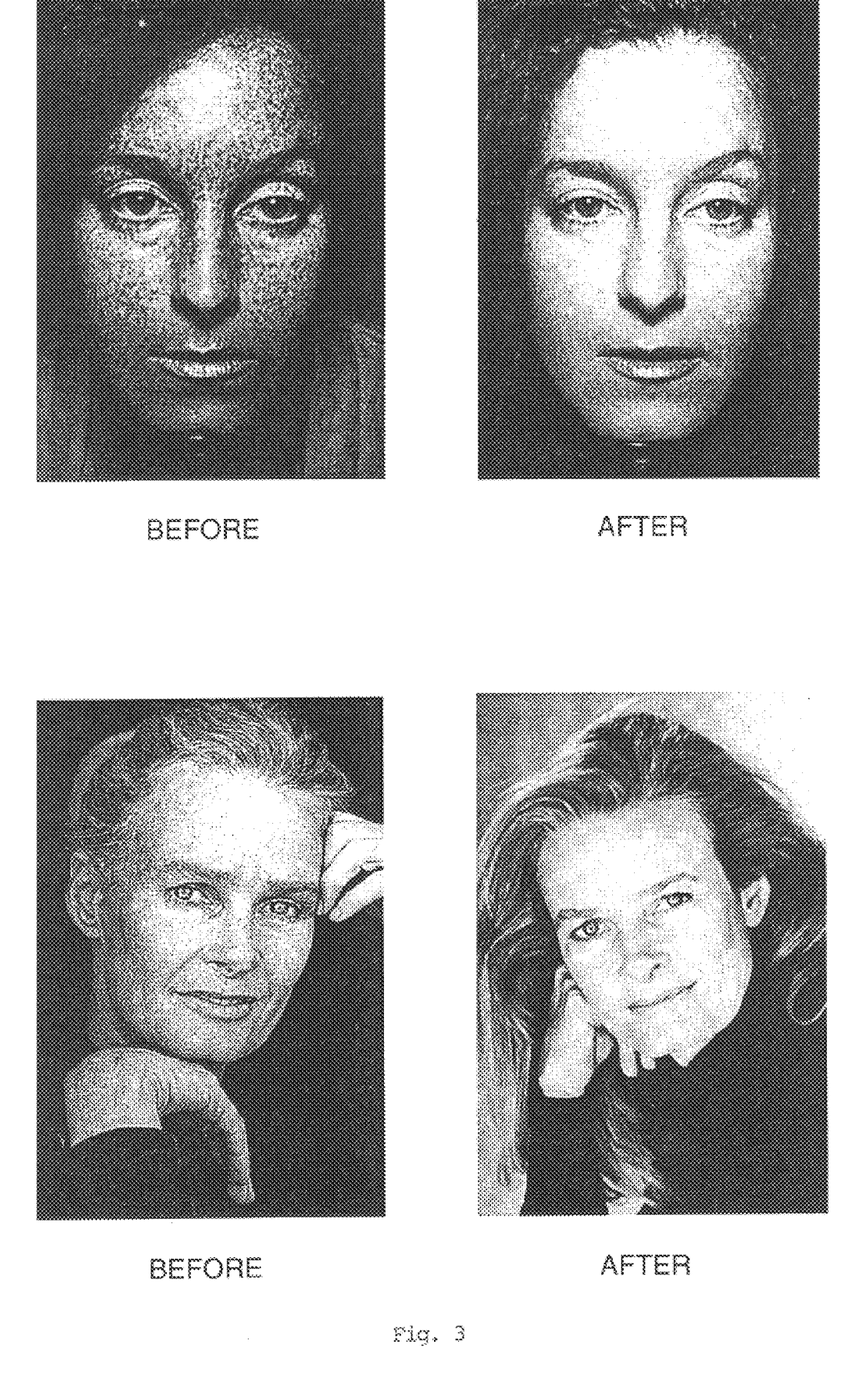
FIG. 3 depicts before and after results on faces following administration of one of the topical compositions set forth in Examples 2–6.
Figure 4:
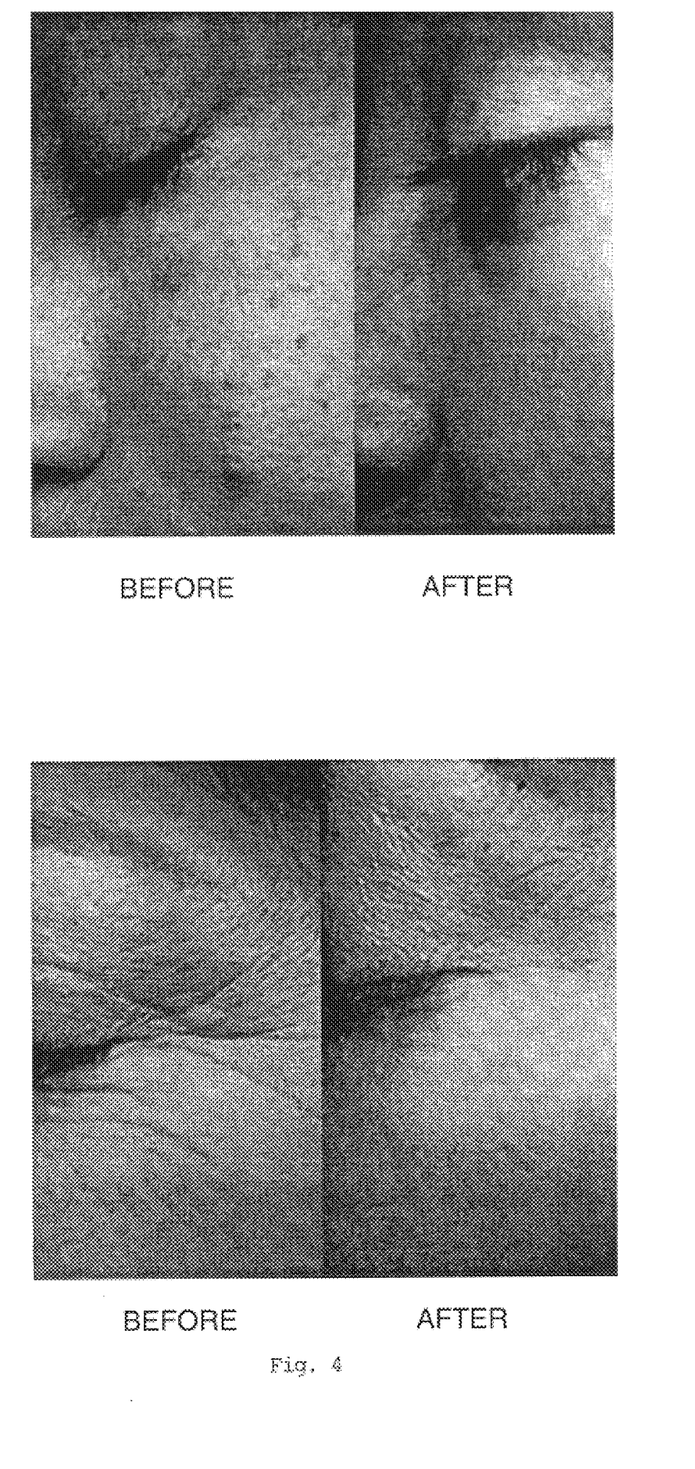
FIG. 4 depicts before and after results on faces following administration of one of the topical compositions set forth in Examples 2–6.
Figure 5:
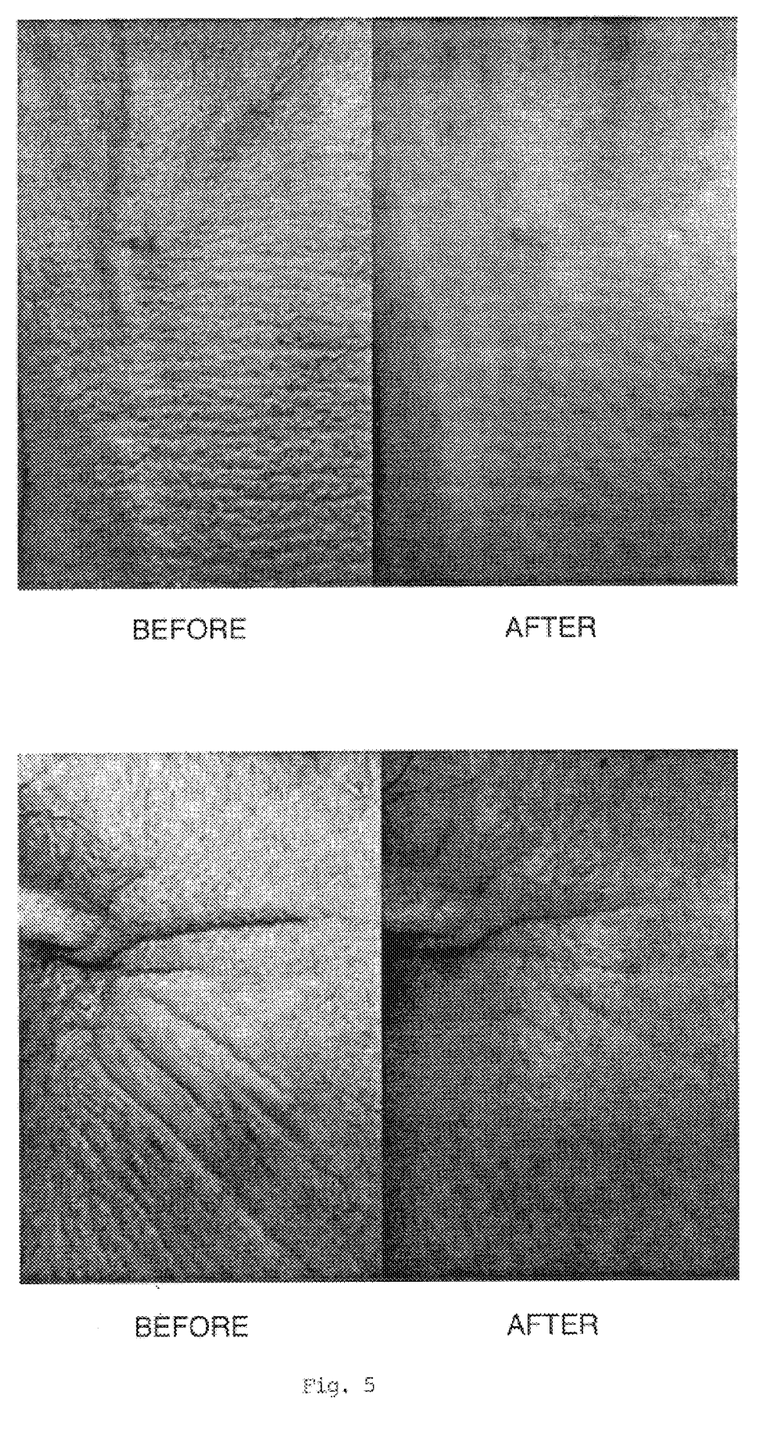
FIG. 5 depicts before and after results on facial skin following administration of one of the topical compositions set forth in Examples 2–6.
Figure 9:
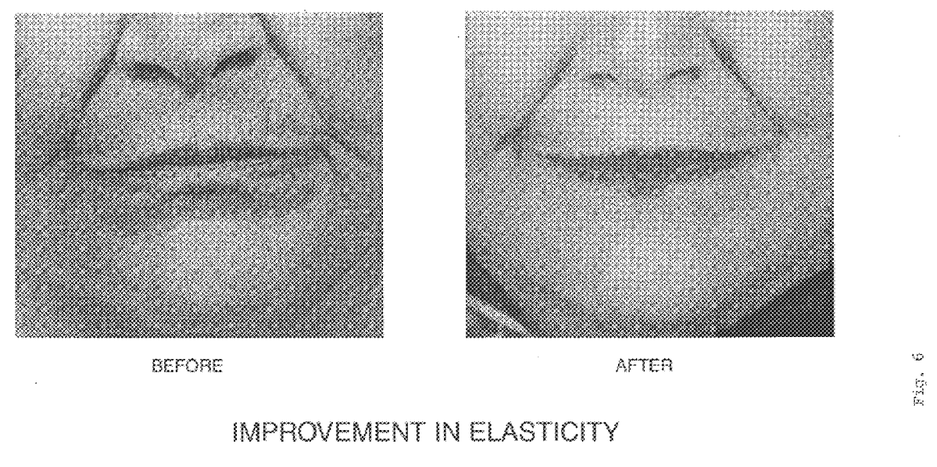

In another study using the Anti-Aging Moisture Concentrate set forth in Example 1 above, the neck of one patient showed dramatic results, according to side by side comparisons of treated vs. untreated skin of the neck. The patient then went on to treat the untreated side, which was the left side, and this also showed the dramatic improvement seen on the previously treated right side. See FIG. 2.

There was also unexplained improvement in the elasticity in a right to left comparison. See FIG. 2 which are photographs that were taken of a pinch test of the skin. On the treated right side of the neck, pinching of the skin revealed very little and difficulty in pinching up any loose skin, and the untreated left side of the neck, skin was easily pinched up to a much greater degree and the skin fold was larger.

EXAMPLE 10

In order to test the effectiveness of the Sacred Lotus Seed Extract when combined with other ingredients another study was done. Two different groups were given the various formulations containing Sacred Lotus seed extract, as set forth in Examples 2–6 set forth above, to use for twelve weeks. The first panel consisted of eight professional models. The second used fourteen women employed in other occupations. The third is a combination of the two. See Tables 1, 2 and 3, respectively. Tables 4, 5, 6 and 7 concern Leaf Width of Germinated Seeds, L-Isoaspartyl Methyl transferase, Steroconfigutation of Aspartyl Residues and Age Determinations, respectively. More particularly, Table 4 illustrates leaf growth of the 332 year old Sacred Lotus seed compared to a 10 year old plant. Table 5 reports the results of methyltransferase assay on a ca 416, 95 and 10 year old Sacred Lotus seeds and fresh Yellow Lotus seeds. Table 6 shows measures of aspartyl residues in L & D configurations of the seeds used in Table 5. Table 7 lists ages of the old Sacred Lotus seeds that can still germinate and reports the methods used.

The Dermatologist noted dramatic improvements in the patients using the formulas containing Sacred Lotus Seed Extract. The formulas increased elasticity, reduced visible pore size, promoted a more refined skin texture, reduced the appearance of crow's feet, lines and wrinkles, reduces blemishes, lightened dark spots promoted firmer, younger looking skin. See FIGS. 3, 4, 5 and 6.

The left column lists the various categories sought to be improved, for example brown spots, blemishes, smaller pores, etc. The next columns give the results of the panel members. The last column is the average percent improvement of the responses given in each category. The top row identifies the participant by number. The bottom row gives overall result of the improvement. Some items are blank because no improvement was needed in that particular category.

TABLE 1

PANEL SURVEY MODELS

| IMPROVEMENT | 1 | 2 | 3 | 4 | 5 | 6 | 7 | 8 | AVERAGE % |
|---|---|---|---|---|---|---|---|---|---|
| BROWN SPOTS | 80 | | 90 | 100 | 90 | 80 | 100 | 70 | 87.10% |
| LESS BLEMISHES | 80 | | 90 | 70 | 90 | 90 | 100 | 100 | 88.60% |
| SMALLER PORES | 100 | 90 | 90 | 80 | 80 | 90 | 100 | 100 | 91.30% |
| MOUTH WRINKLES | 80 | | 90 | 100 | 90 | 80 | 100 | 80 | 88.60% |
| CROWS FEET | 80 | 100 | 100 | 80 | 80 | 80 | 100 | 90 | 88.60% |
| LINES FOREHEAD | 80 | 80 | 90 | 90 | 80 | 80 | 100 | 90 | 86.30% |
| TEXTURE | 90 | | 90 | 100 | 100 | 100 | 100 | 100 | 97.10% |
| MOISTURE | 90 | | 90 | 100 | 70 | 90 | 100 | 80 | 88.60% |
| SMOOTHER SOFTER | 90 | 100 | 90 | 100 | 100 | 100 | 100 | 100 | 97.50% |
| LESS ROUGHNESS | 80 | 100 | 90 | 100 | 100 | 80 | 100 | 100 | 93.80% |
| RADIANCE | 90 | 100 | 100 | 100 | 100 | 100 | 100 | 90 | 97.50% |
| YOUNGER LOOKING | 80 | 100 | 100 | 100 | 100 | 100 | 100 | 90 | 96.30% |
| DIFFERENCES | 100 | 90 | 90 | 100 | 100 | 90 | 100 | 100 | 96.30% |

TABLE 2

MDR PANEL SURVEY

| IMPROVEMENT | 1 | 2 | 3 | 4 | 5 | 6 | 7 | 8 | 9 | 10 | 11 | 12 | 13 | 14 | AVERAGE % |
|---|---|---|---|---|---|---|---|---|---|---|---|---|---|---|---|
| BROWN SPOTS | 80 | 100 | 80 | 90 | 80 | 90 | 100 | 90 | 70 | 70 | 90 | 90 | 70 | | 84.60% |
| LESS BLEMISHES | 80 | 100 | 70 | 70 | 90 | 90 | 100 | 80 | 90 | 70 | 70 | 80 | 100 | | 83.80% |
| SMALLER PORES | 80 | 100 | 80 | 90 | 90 | 90 | 100 | 90 | 90 | 90 | 90 | 100 | 100 | | 91.50% |
| MOUTH WRINKLES | 90 | 100 | 80 | 90 | 90 | | | 70 | 70 | 90 | 100 | 90 | 90 | | 87.30% |
| CROWS FEET | | 100 | 80 | 90 | 90 | | | 70 | 70 | 90 | 90 | 90 | 100 | | 87.00% |
| LINES FOREHEAD | 80 | 100 | 80 | 90 | 90 | 90 | | 80 | 70 | 90 | 90 | 90 | 90 | | 86.70% |
| TEXTURE | 90 | 100 | 90 | 100 | 100 | 90 | | 100 | 90 | 90 | 90 | 80 | 100 | 100 | 93.80% |
| MOISTURE | 100 | 100 | 90 | 90 | 90 | 90 | | 90 | 100 | 90 | 100 | 80 | 100 | 100 | 93.80% |
| SMOOTHER SOFTER | 100 | 100 | 90 | 90 | 90 | 90 | 100 | 100 | 100 | 100 | 90 | 80 | 100 | 100 | 95.00% |
| LESS ROUGHNESS | 100 | 100 | 80 | 90 | 90 | 90 | | 100 | 90 | 100 | 90 | 80 | 100 | 100 | 92.30% |
| RADIANCE | 90 | 100 | 80 | 100 | 100 | 90 | 100 | 100 | 90 | 100 | 100 | 90 | 100 | 100 | 95.70% |
| YOUNGER LOOKING | 80 | 100 | 90 | 90 | 90 | 90 | | 100 | 90 | 100 | 100 | 90 | 100 | 100 | 93.80% |
| OVERALL DIFFERENCES | 90 | 100 | 90 | 100 | 100 | 90 | 100 | 100 | 90 | 90 | 100 | 90 | 100 | 100 | 95.70% |

TABLE 3

PANEL SURVEY TOTAL

| IMPROVEMENT | 1 | 2 | 3 | 4 | 5 | 6 | 7 | 8 | 9 | 10 | 11 | 12 |
|---|---|---|---|---|---|---|---|---|---|---|---|---|
| BROWN SPOTS | 80 | 100 | 80 | 90 | 80 | 90 | 100 | 90 | 70 | 70 | 90 | 90 |
| LESS BLEMISHES | 80 | 100 | 70 | 70 | 90 | 90 | 100 | 80 | 90 | 70 | 70 | 80 |
| SMALLER PORES | 80 | 100 | 80 | 90 | 90 | 90 | 100 | 90 | 90 | 90 | 90 | 100 |
| MOUTH WRINKLES | 90 | 100 | 80 | 90 | 90 | | | 70 | 70 | 90 | 100 | 90 |
| CROWS FEET | | 100 | 80 | 90 | 90 | | | 70 | 70 | 90 | 90 | 90 |
| LINES FOREHEAD | 80 | 100 | 80 | 90 | 90 | 90 | | 80 | 70 | 90 | 90 | 90 |
| TEXTURE | 90 | 100 | 90 | 100 | 100 | 90 | | 100 | 90 | 90 | 90 | 80 |
| MOISTURE | 100 | 100 | 90 | 90 | 90 | 90 | | 90 | 100 | 90 | 100 | 80 |
| SMOOTHER SOFTER | 100 | 100 | 90 | 90 | 90 | 90 | 100 | 100 | 100 | 100 | 90 | 80 |
| LESS ROUGHNESS | 100 | 100 | 80 | 90 | 90 | 90 | | 100 | 90 | 100 | 90 | 80 |
| RADIANCE | 90 | 100 | 80 | 100 | 100 | 90 | 100 | 100 | 90 | 100 | 100 | 90 |
| YOUNGER LOOKING | 80 | 100 | 90 | 90 | 90 | 90 | | 100 | 90 | 100 | 100 | 90 |
| OVERALL DIFFERENCES | 90 | 100 | 90 | 100 | 100 | 90 | 100 | 100 | 90 | 90 | 100 | 90 |

| IMPROVEMENT | 13 | 14 | 15 | 16 | 17 | 18 | 19 | 20 | 21 | 22 | AVERAGE % |
|---|---|---|---|---|---|---|---|---|---|---|---|
| BROWN SPOTS | 70 | | 80 | | 90 | 100 | 90 | 80 | 100 | 70 | 85.50% |
| LESS BLEMISHES | 100 | | 80 | | 90 | 70 | 90 | 90 | 100 | 100 | 85.50% |
| SMALLER PORES | 100 | | 100 | 90 | 90 | 80 | 80 | 90 | 100 | 100 | 91.40% |
| MOUTH WRINKLES | 90 | | 80 | | 90 | 100 | 90 | 80 | 100 | 80 | 87.80% |
| CROWS FEET | 100 | | 80 | 100 | 100 | 80 | 80 | 80 | 100 | 90 | 87.80% |
| LINES FOREHEAD | 90 | | 80 | 80 | 90 | 90 | 80 | 80 | 100 | 90 | 86.50% |
| TEXTURE | 100 | 100 | 90 | | 90 | 100 | 100 | 100 | 100 | 100 | 95.00% |
| MOISTURE | 100 | 100 | 90 | | 90 | 100 | 70 | 90 | 100 | 80 | 92.00% |
| SMOOTHER SOFTER | 100 | 100 | 90 | 100 | 90 | 100 | 100 | 100 | 100 | 100 | 95.90% |
| LESS ROUGHNESS | 100 | 100 | 80 | 100 | 90 | 100 | 100 | 80 | 100 | 100 | 92.90% |
| RADIANCE | 100 | 100 | 90 | 100 | 100 | 100 | 100 | 100 | 100 | 90 | 96.40% |
| YOUNGER LOOKING | 100 | 100 | 80 | 100 | 100 | 100 | 100 | 100 | 100 | 90 | 94.80% |
| OVERALL DIFFERENCES | 100 | 100 | 100 | 90 | 90 | 100 | 100 | 90 | 100 | 100 | 95.90% |

TABLE 4

Leaf Width* of Sacred Lotus, SL (*Nelumbo nucifera*).

| FRUIT | DAY | 3rd | 4th | 5th N1 | 6th N2 | 7th N1a (mm) | 8th Pb | 9th N3 | 10th N4 | 11th N5 |
|---|---|---|---|---|---|---|---|---|---|---|
| ~332 Yr-Old (oSL) | | | | | | | | | | |
| oSL5 | 16 | E | | | | | | | | |
| | 20 | F | | | | | | | | |
| | 23 | 14.0 | E | | | | | | | |
| | 36 | 44.0 | 53.2 | E | | | | | | |
| | 43 | 44.0 | 57.0 | 67.0 | E | | | | | |
| | 50 | 44.0 | 57.5 | 87.0 | 64.0 | | | | | |
| | 55 | 43.0 | 58.0 | 86.0 | 99.0 | — | — | E | | |
| 10 Yr-Old (dSL) | | | | | | | | | | |
| dSL8 | 50 | 83.0 | 95.8 | 117 | E | E | E | | | |
| | 56 | 85.0 | 96.0 | 120 | 130 | F | F | E | | |
| | 68 | 85.0 | 95.0 | 120 | 162 | 96.0 | 47.5 | 165 | E | E |
| | 73 | 86.0 | 95.0 | 121 | 163 | 100 | 48.0 | 183 | F | F |
| | 81 | 85.0 | 95.0 | 122 | 164 | 103 | 46.0 | 186 | 99.0 | 126 |
| dSL 10** | 50 | 61.0 | 65.0 | 85 | F | | | | | |
| | 56 | 61.0 | 64.0 | 82 | 130 | — | — | E | | |
| | 68 | 63.0 | 66.0 | 131 | 127 | 81.5 | — | F | E | |
| | 73 | 54.0 | 56.0 | 132 | 143 | 84.0 | — | F | F | |
| | 81 | dead | 56.0 | 131 | 148 | 84.0 | — | F | F | 78.0 |

*Largest width of leaf ("tip-to-tip" measurement); N - node; N1a - 2nd leaf of node 1; Pb - leaf at plumule base; E - emerging leaf; F - folded leaf.
**Cotyledon tips removed (48 h after imbibition) for methyltransferase assay (see Table 5).

TABLE 5

L-isoaspartyl Methyltransferase in Cotyledons and Embryonic Axes of
Sacred Lotus (SL, *Nelumbo nucifera*) and Yellow Lotus (YL, *N. lutea*).

| | | METHYLTRANSFERASE (pmol/min/mg protein) | | |
| --- | --- | --- | --- | --- |
| | | COTYLEDONS | | |
| FRUIT | IMBIBITION (hr) | TIP HALF | BASE HALF | EMBRYONIC AXES |
| OLD SL (oSL) | | | | |
| 6 (~416 yr) | 22 (d) | 0.19 | 0.28 | 0.44 |
| 7 (~95 yr) | no | 0.12 | 0.39 | 0.73 |
| AVE + σ | | 0.16 + 0.04 | 0.34 + 0.06 | 0.59 + 0.15 |
| 10 Yr-OLD SL (dSL)* | | | | |
| 10 | 5 | 0.16 | NA | NA |
| 11 | 48 | 0.02 | NA | NA |
| I    12 | 5 | 0.26 | NA | NA |
| 13 | 48 | 0.05 | NA | NA |
| 14** | no | 0.59 | NA | 1.43 |
| 15 | no | 0.40 | NA | 0.72 |
| 16 | no | 0.16 | 0.43 | 0.62 |
| 17 | no | 0.14 | 0.37 | 0.76 |
| II   18 | 5 | 0.10 | 0.30 | 0.59 |
| 19 | 5 | 0.20 | 0.26 | 0.74 |
| 20 | 48 | 0.15 | 0.31 | 0.70 |
| 21 | 48 | 0.12 | 0.21 | 0.67 |
| AVE (II) + σ | | 0.14 + 0.01 | 0.31 + 0.03 | 0.68 + 0.03 |
| FRESH YL (fYL) | | | | |
| 5 | no | 0.31 | 0.21 | 0.48 |
| 6 | no | 0.13 | 0.21 | 0.52 |
| 7 | 5 | 0.28 | 0.17 | 0.40 |
| 8 | 5 | 0.16 | 0.24 | 0.57 |
| 9 | 48 | 0.27 | 0.26 | 0.55 |
| 10 | 48 | 0.20 | 0.17 | 0.72 |
| AVE + σ | | 0.22 + 0.03 | 0.21 + 0.01 | 0.54 + 0.04 |

*Two experiments (I, II).
**Unhealthy cotyledons and plumules, and probably damaged pericarp.
NA: not analyzed.

TABLE 6

Stereoconfiguration of Aspartyl Residues in Hydrolysates of Proteins of Seeds of
Sacred Lotus (SL, *Nelumbo nucifera*) and Yellow Lotus (YL, *N. lutea*).

| | D-ASP | | L-ASP | |
| --- | --- | --- | --- | --- |
| FRUIT | COTYLEDON* | EMBRYONIC | COTYLEDON* | EMBRYONIC |
| | | (Mol %) | | |
| OLD SL (oSL) | | | | |
| oSL6 | 1.67 | 1.26 | 98.3 | 98.7 |
| oSL7 | 1.76 | 1.50 | 98.2 | 98.5 |
| AVE + σ | 1.72 + 0.04 | 1.38 + 0.12 | 98.2 + 0.05 | 98.6 + 0.1 |
| 10 Yr-OLD SL (dSL) | | | | |
| dSL14 | 2.13 | 2.04 | 97.9 | 98.0 |
| dSL16 | 1.66 | 1.52 | 98.3 | 98.5 |
| AVE + σ | 1.90 + 0.23 | 1.78 + 0.26 | 98.1 + 0.2 | 98.2 + 0.2 |
| FRESH YL (fYL) | | | | |
| fYL5 | 1.69 | 1.52 | 98.3 | 98.5 |
| fYL9 | 2.43 | 2.24 | 97.6 | 97.8 |
| AVE + σ | 2.06 + 0.37 | 1.88 + 0.36 | 98.0 + 0.4 | 98.2 + 0.4 |

*Cotyledon tissues from the base half

TABLE 7

Age Determinations* Reported by Various Laboratories of Sacred Lotus (*Nelumbo nucifera*)
from the Dry Lake Bed at Pulantien on Liaotung Peninsula, Northeastern China.

| RADIOCARBON AGE (yr BP) | CALENDAR RANGE A.D. | MEAN PHYSICAL AGE (yr) | TISSUE USED IN RADIOCARBON DATING (DRY OR GERMINATION TESTED) | REFERENCE |
|---|---|---|---|---|
| | | | Ohga Collection♦ (1923) | |
| 100 ± 60** | 1682–1807 | 256 ± 62 | Charred residue | Godwin and Willis, 1964 |
| 1040 ± 210** | 770–1218 | 1,000 ± 224 | Fruit (dry) | Libby, 1955 |
| | | | Chinese Collection (1952) | |
| 40 ± 60 | 1887–1911 | 95 ± 12 | Pericarp (dry fruit) | Shen-Miller et al., 1994, this paper |
| 270 ± 60 | 1527–1797 | 332 ± 135 | Pericarp (germinated seed) | Shen-Miller et al., 1994, this paper |
| 300 ± 60 | 1495–1660 | 416 ± 82 | Pericarp (ungerminated seed) | Shen-Miller et al., 1994, this paper |
| 340 ± 80 | 1447–1653 | 444 ± 103 | Fruit (ungerminated) | Priestly and Posthumus, 1982 |
| 430 ± 100 | 1414–1631 | 471 ± 108 | Fruit (germinated) | Priestly and Posthumus, 1982 |
| 705 ± 145 | 1212–1409 | 684 ± 99 | Fruit (germinated) | Shen-Miller et al., 1994, this paper |
| 740 ± 185 | 1069–1409 | 755 ± 170 | Fruit (ungerminated) | Shen-Miller et al., 1994, this paper |
| 915 ± 80 | 1023–1217 | 874 ± 97 | Fruit (dry) | Chang, 1978 |
| 1350 ± 220 | 434–977 | 1,288 ± 271 | Fruit (germinated) | Shen-Miller et al., 1994, this paper |

*Radiocarbon age ± σ(yr BP) based on the determined $^{14}C$ content of the lotus fruit or pericarp and the $^{14}C$ half-life of 5568 ± 30 yr (Libby, 1955), and following the conventions of Stuvier and Polach (1977); yr BP: years before present (before 1950); calendar range obtained from the A.D. range extrapolated from the $^{14}C$ decadal calibration curve of Stuvier and Becker (1993), discarding those ranges that fall after the lotus collection dates: mean physical age based on the mean age deduced from the calendar A.D. range.
**Godwin and Willis re-dated the charred residue of Libby's fruit, originally dated as ~1,040 yr BP.
♦Ohga, based on available geologic and historical records, estimated his Pulantien collection of the lotus fruits as ~400 yr in age (Wester, 1973).

The present invention may, of course, be carried out in other specific ways than those herein set forth without departing from the spirit and essential characteristics of the present invention. The present embodiments are, therefore, to be considered in all respects as illustrative and not restrictive and all changes coming within the meaning and equivalency range of the appended claims are intended to be embraced herein.

Having described our invention, we claim:

1. A method of treating the skin of a human, said method comprising administering to the human an anti-aging component in an amount effective to treat the skin, wherein the anti-aging component is combined with at least one acceptable vehicle to form a delivery system, the delivery system being an oral composition and the anti-aging component comprising methyltransferase.

2. The method of claim 1, wherein the delivery system further comprises a topical composition.

3. The method of claim 1, wherein said administration comprises ingesting an effective amount of the oral composition.

4. The method of claim 1, the delivery system further including ascorbic acid and glutathione.

5. The method of claim 1, wherein the methyltransferase is L-isoaspartyl methyltransferase.

6. The method of claim 1, wherein the anti-aging component is an extract of a Sacred Lotus seed.

7. The method of claim 1, wherein the anti-aging component is derived from components of a Sacred Lotus plant.

8. The method of claim 1, wherein the anti-aging component is derived from ground Sacred Lotus seeds.

9. The method of claim 1, wherein the anti-aging component is derived from a source selected from the group consisting of components of a Yellow Lotus plant, Yellow Lotus seed, wheat germ oil, animal liver, animal brain and animal testes.

10. The method of claim 1, whereby the method reduces, eliminates prevents or reverses signs of aging of the skin.

11. The method of claim 10, wherein the signs of aging of the skin are selected from the group consisting of loss of elasticity, age spots, acne, blemishes, enlarged pores, discoloration, fine lines and wrinkles.

12. The method of claim 1, whereby the method restores the skin to a more youthful appearance.

13. The method of claim 1, whereby the method reduces damage to the skin caused by aging.

14. The method of claim 1, whereby the method treats acne.

* * * * *